United States Patent
Subramaniam et al.

(10) Patent No.: US 6,353,126 B1
(45) Date of Patent: Mar. 5, 2002

(54) PROCESS FOR THE PRODUCTION OF MALONONITRILE

(75) Inventors: Chitoor S. Subramaniam; Zheng Wang, both of East Brunswick, NJ (US)

(73) Assignee: Creanova Inc., Somerset, NJ (US)

( * ) Notice: Subject to any disclaimer, the term of this patent is extended or adjusted under 35 U.S.C. 154(b) by 0 days.

(21) Appl. No.: 09/345,304

(22) Filed: Jun. 30, 1999

(51) Int. Cl.$^7$ ............................................. C07C 253/14
(52) U.S. Cl. ....................................... 558/312
(58) Field of Search ......................... 558/312

(56) References Cited

U.S. PATENT DOCUMENTS

| | | |
|---|---|---|
| 3,511,869 A | 5/1970 | Rosin |
| 4,105,688 A | 8/1978 | Arni et al. |

FOREIGN PATENT DOCUMENTS

| | | |
|---|---|---|
| JP | 57203051 | 12/1982 |

OTHER PUBLICATIONS (a) Freeman, F. *Chem Rev.* 69 (5) 591 1969, (b) Fatiadi, A. J. *Synthesis* 165–204 1978, (c) Freeman, F. *Chem. Rev.* 329–350 1980, (d) Freeman, F. *Synthesis* 925–954 1981.

(a) Surrey, A.R. *Organic Synthesis* Col. vol. III, John Wiley and Sons, Inc., New York, NY., 53 1955, (b) Corson, B.B. Scott, R.W. Vose, C.E. *Organic Synthesis* Coll. vol. II, John Wiley and Sons, Inc., New York, NY, P379 1943.

Olah, G.A. et al. *Synthesis* 657–658 1980.

*Primary Examiner*—Floyd D. Higel
*Assistant Examiner*—Ebenezer Sackey
(74) *Attorney, Agent, or Firm*—Abelman, Frayne & Schwab

(57) ABSTRACT

An improved process for the commercial production of malononitrile by the dehydration of cyanoacetamide employs cyanuric chloride in the presence of a catalytic amount of N,N-dimethylformamide and in a polar solvent that is removed by vacuum distillation at a temperature below 100° C. The N,N-dimethylformamide is added in a molar ratio of 0.16 moles for each mole of cyanoacetamide present in the starting solution.

13 Claims, No Drawings

PROCESS FOR THE PRODUCTION OF MALONONITRILE

FIELD OF THE INVENTION

The present invention relates to an improved process for the commercial production of malononitrile.

BACKGROUND OF THE INVENTION

Malononitrile is a versatile compound of exceptional reactivity that makes it one of the most important organic intermediates used in research and in the chemical industry. It is a keystone in the syntheses of pharmaceuticals, dyestuffs, pesticides, fungicides and a variety of polymers.

Malononitrile has been commercially produced by the reaction of cyanogen chloride with acetonitrile in a cylindrical reactor at about 750° C. There are certain disadvantages associated with this process: first, the high operating temperature requires a heat-resistant apparatus that is expensive to construct and to operate; and secondly, the malononitrile reaction product is contaminated with by-products such as carbon and polymers that are difficult to separate and which increases the cost associated with the product.

Malononitrile has also been produced commercially by a process that includes the dehydration of cyanoacetamide with phosphorous pentachloride and other phosphorous compounds. However, a major drawback of this process is that it produces relative large quantity of phosphate waste as a by-product.

Japanese patent publication 57 203051 discloses that malononitrile can be prepared by treating cyanoacetaldehyde dimethyl acetal, $NCCH_2CH(OCH_3)_2$, with an aqueous solution, followed by reaction with hydroxylamine-O-sulfonic acid, $H_2NOSO_3H$. However, the disposal of the acid waste generated by this process would constitute a major drawback to its commercial use.

It is known from Olah et als.' publication in *Synthesis* (1980, 657–58) that cyanuric chloride is useful as a mild dehydrating agent in the preparation of nitrites from amides when the reaction was carried out in N,N-dimethylformamide as a solvent. However, the method as disclosed by Olah et al. does not lend itself to the commercial production of malononitrile due to the fact that the N,N-dimethylformamide has a relatively high boiling point and an inclusion complex, or adduct, is formed during the separation step when the temperature exceeds about 100° C. Thus, when the mixture of the highly reactive malononitrile and N,N-dimethylformamide reaches about 100° C. the compounds react to form the adduct which prevents further malononitrile from being isolated and recovered from the reaction mixture. As a result, the relatively low yield of malononitrile and processing and disposal problems associated with the adduct by-product [c.f., Moetz & Rodriguez, *Tetra. Letters*, Vol. 38, No. 24, pp. 4221–22 (1997)] renders the dehydration process as described by Olah et al. of no commercial significance.

It is therefore an object of this invention to provide an improved process for the commercial production of malononitrile that can be carried out under mild conditions, i.e., in a process that does not require extremes of temperature and/or pressure.

Another object of the invention is to provide a novel process for the production of malononitrile in improved yields and without the production of by-products, the disposal of which are difficult and expensive.

Yet another object of this invention is to provide an improved commercial process in which the malononitrile end product is easily separated from the reaction mixture.

SUMMARY OF THE INVENTION

What has been found is that N,N-dimethylformamide functions in relatively small amounts and under mild conditions as a dehydration catalyst when cyanuric chloride is employed as a dehydration agent for cyanoacetamide.

In accordance with the invention, malononitrile is synthesized by reacting cyanoacetamide and cyanuric chloride in the presence of a catalytic amount of N,N-dimethylformamide ("DMF") in accordance with the reaction scheme.

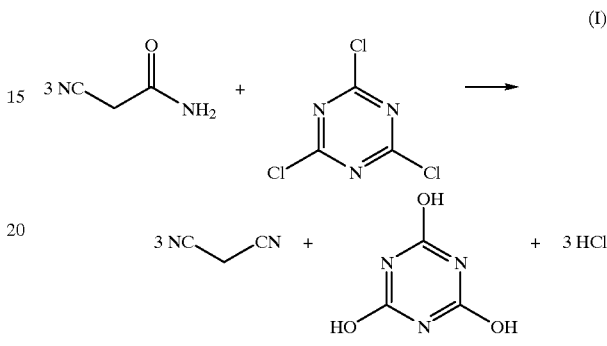

The reaction is preferably carried out in a polar solvent in which the cyanoacetamide is readily soluble. A preferred polar solvent is acetonitrile. Suitable polar solvents in addition to acetonitrile include tetrahydrofuran, 1,4-dioxane, and ethylacetate.

The reaction is conducted at a temperature in the range of from 10° C. to 100° C., and preferably in the range of from about 50° C. to about 80° C., and most preferably in the range of from about 50° C. to about 60° C.

The advantages of this process are as follows: first, the dehydration reaction is carried out under relatively mild conditions of temperature and pressure; second, malononitrile is synthesized in good yields and can easily be separated from the reaction mixture; and third, there is no phosphate waste or other by-product generated by the process. Moreover, the process of the invention has the additional benefit that the DMF can be recovered for reuse.

This reaction scheme avoids the drawbacks of the process disclosed by Olah et al. by the use of a polar solvent for the cyanoacetamide that (1) has a relatively low boiling point to facilitate its removal and recovery for reuse; and (2) does not react with the malononitrile, thereby increasing the yield of the desired product.

DETAILED DESCRIPTION OF THE INVENTION

In accordance with the novel process of the invention, malononitrile is synthesized by reacting the equivalent of one mole of cyanoacetamide and 0.42 mole-equivalents of cyanuric chloride in the presence of a catalytic amount of N,N-dimethylformamide. The DMF can be present in the range of from about 0.05 mol to about 0.30 mol, and preferably in a range from about 0.10 mol to about 0.20 mol, based on one mole of cyanoacetamide, the most preferred amount being 0.16 mol per mole of cyanoacetamide, for practice of the process under the conditions of temperature and pressure identified above and in the examples which follow. Thus, the optimum molar equivalents are 0.42 mol of cyanuric chloride and 0.16 mol of N,N-dimethylformamide per mole of cyanoacetamide.

The reaction is carried out in a polar solvent, preferably acetonitrile, in accordance with the reaction scheme of equation (I), above. The reaction mixture is maintained at a temperature in the range from 10° C. to 100° C., and preferably in the range from 50° C. to 80° C., and most preferably in the range from 50° C. to about 60° C.

In a preferred embodiment, the cyanoacetamide is first dissolved in the solvent, which step, for convenience, can be completed by adding the solvent, e.g., acetonitrile, to the reaction vessel and adding the crystalline cyanoacetamide to the acetonitrile solvent with stirring. Since both compounds are flammable and the acetonitrile, or methyl cyanide, is toxic by skin absorption, the reaction is conducted under a nitrogen atmosphere in accordance with well-known standard industry practice.

The cyanoacetamide solution is maintained at a temperature in the range of about 50° C.–60° C. by a heated water jacket or a thermostatically controlled electrical heater.

After the cyanoacetamide is completely dissolved in the solvent, the cyanuric chloride is added slowly to the reaction vessel, the contents of which are continuously stirred. Simultaneously, the catalyst N,N-dimethylformamide is slowly added to assure thorough mixing of the reactants. The addition of the second reactant and proportional addition of the catalyst is preferably completed over a period of 5 to 7 hours. The reaction is exothermic and the temperature of the stirred reactants rises and should not be allowed to exceed a temperature of 100° C. in the vessel in order to avoid decomposition of the product. Hydrogen chloride gas generated during the reaction is removed by any convenient means, e.g., absorption in a base trap containing caustic.

After catalyst addition is complete, the contents of the vessel are stirred for approximately another five (5) hours while maintaining the temperature in the range of from about 50° C. to 60° C. After addition of the catalyst and cyanuric chloride has been completed, the progress of the reaction is monitored by gas chromatographic ("GC") analysis.

When the reaction has proceeded to the desired degree of completion as determined by GC, the reaction mixture is filtered, the precipitate being cyanuric acid which is recovered and air dried. This material can be used as an antifouling agent and has utility as a marine biocide. The recovery of this material as a by-product having industrial utility, rather than a waste stream requiring treatment for environmentally acceptable disposal, is another commercially important aspect of the invention.

The filtrate is concentrated, as by heating under vacuum at about 200 mm Hg and the malononitrile is recovered in purified form by vacuum distillation. The yield, which is dependent upon the solvent employed, will be in the range of from about 50% to about 75% in the commercial-scale practice of the process.

The following examples are provided to illustrate the effect of increasing the amount of the catalyst N,N-dimethylformamide on the yield of malononitrile and the use of several solvents. As noted, Example 5 is a comparative example in which the N,N-dimethylformamide is employed as a solvent, and in a quantity that far exceeds the optimum molar range of 0.05 to 0.30 mol, and the preferred about of 0.16 mol equivalents, based on cyanoacetamide.

EXAMPLE 1

A 250 ml three-neck round bottom flask equipped with central mechanical stirring and a thermometer is provided with a hot water jacket maintained at about 50°–60° C. The flask is also provided with a dry nitrogen atmosphere. To the flask is added 50 ml of acetonitrile in which 16.8 grams (0.2 mol) of cyanoacetamide is dissolved. Thereafter, there are slowly added to the flask in separate streams, 15.54 grams (0.084 mol) of cyanuric chloride and 2.5 ml of N,N-dimethylformamide (0.32 mol, which is 0.16 mol equivalent). The cyanuric chloride and N,N-dimethylformamide are added simultaneously over a period of about 5–7 hours. The reaction mixture is stirred for an additional 5 hours at 50–60° C., the total reaction time being about 11–12 hours. Hydrogen chloride generated by the reaction is absorbed in a base trap filled with caustic. The progress of the reaction is monitored by GC. When the desired end-point is reached, the reaction mixture is cooled to room temperature and is then filtered; the precipitate of cyanuric acid is air dried. The filtrate is concentrated under vacuum and the DMF is removed by vacuum distillation at a temperature that does not exceed 100° C., to provide a yield of the malononitrile of 9.7 gram (72%) at a purity exceeding 98% (GC analysis).

EXAMPLE 2

In a 250 ml three-neck flask equipped as described in Example 1, 8.4 grams (0.1 mol) of cyanoacetamide is dissolved in 20 ml of acetonitrile maintained at about 50–60° C. Thereafter, 6.27 grams (0.034 mol) of cyanuric chloride and 2 ml of N,N-dimethylformamide (0.026 mol) are slowly added over a period of about 1–2 hours. The reaction mixture is stirred for another 10 hours at a temperature in the range of from 50–60° C. (total reaction time about 11–12 hours). Hydrogen chloride generated by the reaction is absorbed in a base trap filled with caustic. The reaction is monitored by GC. The reaction mixture is then filtered and the precipitate of cyanuric acid is air dried. The filtrate is concentrated and malononitrile is purified by vacuum distillation for a yield of 4.44 gram (67%) having a purity 98% (GC).

EXAMPLE 3

In a 250 ml three-neck flask equipped as described in Example 1, 8.4 grams (0.1 mol) of cyanoacetamide is dissolved in 20 ml of ethylacetate maintained at about 50–60° C. Thereafter, 6.27 grams (0.034 mol) of cyanuric chloride and 2 ml of N,N-dimethylformamide (0.026 mol) are slowly added over a period of about 1–2 hours. The reaction mixture is stirred for about another 10 hours at a temperature in the range of from 50–60° C. (total reaction time about 11–12 hours). Hydrogen chloride generated by the reaction is absorbed in a base trap filled with caustic. The reaction is monitored by GC. The reaction mixture is then filtered and the precipitate of cyanuric acid is air dried. The filtrate is concentrated and malononitrile is purified by vacuum distillation for a yield of 3.4 gram (52%) with a purity exceeding 98% (GC).

EXAMPLE 4

In a 250 ml three-neck flask equipped as described in Example 1, 8.4 grams (0.1 mol) of cyanoacetamide is dissolved in 20 ml of 1,4-dioxane maintained at about 50–60° C. Thereafter, 6.27 grams (0.034 mol) of cyanuric chloride and 2 ml of N,N-dimethylformamide (0.026 mol) are slowly added over a period of about 1–2 hours. The reaction mixture is stirred for about another 10 hours at a temperature in the range of from 50–60° C. (total reaction time about 11–12 hours). Hydrogen chloride generated by the reaction is absorbed in a base trap filled with caustic. The reaction is monitored by GC. The reaction mixture is then filtered and the precipitate of cyanuric acid is air dried. The filtrate is concentrated and malononitrile is purified by vacuum distillation for a yield of 2.9 gram (44%) at a purity of 98% (GC).

EXAMPLE 5 (COMPARATIVE EXAMPLE)

Into a stirred three-neck round bottom flask equipped as described in Example 1 and containing 20 ml of N,N-dimethylformamide is added 8.4 grams (0.1 mol) of cyanoacetamide. After the cyanoacetamide is dissolved, 6.27 grams (0.034 mol) of cyanuric chloride which has been previously dissolved in 20 ml tetrahydrofuran is introduced to the flask in small portions over a period of about 1–2 hours. The reaction mixture is maintained at a temperature in the range from 50–60° C. and stirred for approximately another 10 hours (total reaction time about 11–12 hours). Hydrogen chloride generated by the reaction is absorbed in a base trap filled with caustic. The progress of the reaction is monitored by GC until the desired end point is reached. The reaction mixture is cooled to room temperature, filtered and the precipitated cyanuric acid is air dried. The filtrate is concentrated by heating under vacuum at about 200 mm Hg. The malononitrile is recovered and purified by vacuum distillation to provide a yield of 3.51 gram (53%) at a purity exceeding 98% (GC).

Thus it is seen from Examples 1 and 2 that increasing the amount of DMF above the optimum of 0.16 mol equivalents in the same solvent system results in a decrease in the yield of the malononitrile. Examples 4 and 5 employ the same molar quantities of reactants as Example 2, but the reaction is conducted in different solvent systems. When ethylacetate is used as a solvent (Example 3), a yield comparable to that of acetonitrile is obtained; when the solvent is dioxane (Example 4), the yield is lower.

We claim:

1. A method for the production of malononitrile comprising reacting cyanoacetamide and cyanuric chloride in the presence of a catalytic amount of N,N-dimethylformamide in the range of from 0.05 to 0.30 and a solvent that is not N,N-dimethylformamide, and recovering the malononitrile from the reaction mixture.

2. The method of claim 1 where the molar ratio of N,N-dimethylformamide to cyanoacetamide is about 0.10 to 0.20.

3. The method of claim 1 where the reaction is conducted in a polar solvent.

4. The method of claim 3 there the polar solvent is selected from the group consisting of acetonitrile, tetrahydrofuran, ethylacetate and 1,4-dioxane.

5. The method of claim 4 where the polar solvent is acetonitrile.

6. The method of claim 1 where the reaction is conducted at a temperature in the range of from about 10° C. to about 100° C.

7. The method of claim 6 where the reaction is conducted at a temperature in the range from about 50° C. to about 60° C.

8. The method of claim 3 where the cyanoacetamide is dissolved in the polar solvent or the N,N-dimethylformamide prior to addition of the cyanuric chloride.

9. The method of claim 8 where the total quantity of cyanuric chloride added to the reaction mixture does not exceed about 0.42 mol equivalents of the amount of cyanoacetamide originally present in the reaction mixture.

10. The method of claim 1 where the reaction mixture includes a precipitate and the malononitrile is recovered from the reaction mixture by filtration to remove the precipitate and the malononitrile is recovered by concentrating and vacuum distilling the filtrate.

11. The method of claim 10 where the filtrate is vacuum distilled at less than about 5 mm Hg.

12. The method of claim 10 where the precipitate comprises cyanuric acid and the precipitate is dried to recover the cyanuric acid.

13. A process for the synthesis of malononitrile by the dehydration of cyanoacetamide employing cyandric chloride in the presence of N,N-dimethylformamide comprising:

a) dissolving the cyanoacetamide in a low-boiling polar solvent that is not N,N-dimethylformamide;

b) adding the N,N-dimethylformamide to the solution in a ratio of about 0.16 mole for each mole of cyanoacetamide originally present in the solution;

c) adding cyanuric chloride to the solution;

d) maintaining the reaction mixture at a temperature in a range of from about 50 ° C to about 60 ° C until the reaction is complete; and e) recovering malononitrile from the reaction mixture.

* * * * *